(12) United States Patent  
Kressner

(10) Patent No.: US 8,671,492 B2
(45) Date of Patent: Mar. 18, 2014

(54) ELECTRIC TOOTHBRUSH

(75) Inventor: Gerhard Kressner, Altenstadt (DE)

(73) Assignee: Braun GmbH, Kronberg (DE)

( * ) Notice: Subject to any disclaimer, the term of this patent is extended or adjusted under 35 U.S.C. 154(b) by 412 days.

(21) Appl. No.: 12/972,741

(22) Filed: Dec. 20, 2010

(65) Prior Publication Data

US 2011/0083288 A1    Apr. 14, 2011

Related U.S. Application Data

(63) Continuation of application No. PCT/EP2009/004233, filed on Jun. 12, 2009.

(51) Int. Cl.
*A46B 13/02*    (2006.01)

(52) U.S. Cl.
USPC .......................................... 15/22.1

(58) Field of Classification Search
USPC .......................................... 15/22.1
See application file for complete search history.

(56) References Cited

U.S. PATENT DOCUMENTS

| 5,289,604 | A | * | 3/1994 | Kressner | 15/22.1 |
| 6,381,795 | B1 | | 5/2002 | Hofmann et al. | |
| 6,588,042 | B2 | * | 7/2003 | Fritsch et al. | 15/22.1 |
| 6,836,917 | B2 | | 1/2005 | Blaustein et al. | |
| 7,690,067 | B2 | * | 4/2010 | Schaefer et al. | 15/22.1 |

FOREIGN PATENT DOCUMENTS

| DE | 102 09 320 A1 | 9/2003 |
| EP | 0 500 537 A | 9/1992 |
| FR | 2 131 359 A | 11/1972 |
| WO | WO 00/76420 A1 | 12/2000 |
| WO | WO 02/071970 A | 9/2002 |

OTHER PUBLICATIONS

European Search Report dated Nov. 21, 2008.

* cited by examiner

*Primary Examiner* — Randall Chin
(74) *Attorney, Agent, or Firm* — John P. Colbert

(57) ABSTRACT

An attachment part for an electric toothbrush is disclosed. The attachment has a brush head, a tubular connecting piece being connected to the brush head for connecting the same to the head of a toothbrush handle, and a drive shaft for driving the working head. The connecting piece has at least one interior latching element that is arranged such that it is suitable to move into the interior of the neck of the handle and to create a disengageable connection of the attachment part to the neck of the handle, the interior latching element being radially inwardly offset, with regard to the diameter thereof, relative to an internal cylindrical surface of the connecting piece, such that a gap remains between the exterior of the interior latching element and the internal cylindrical surface, the gap being suitably made such that a wall of the neck of the handle can be moved into it.

16 Claims, 17 Drawing Sheets

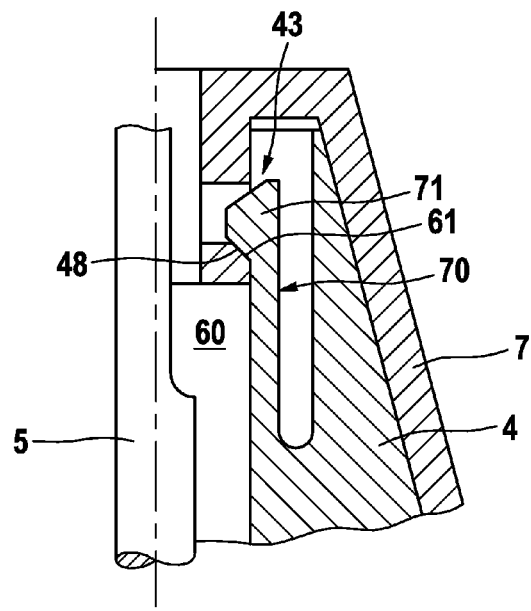
Fig. 9
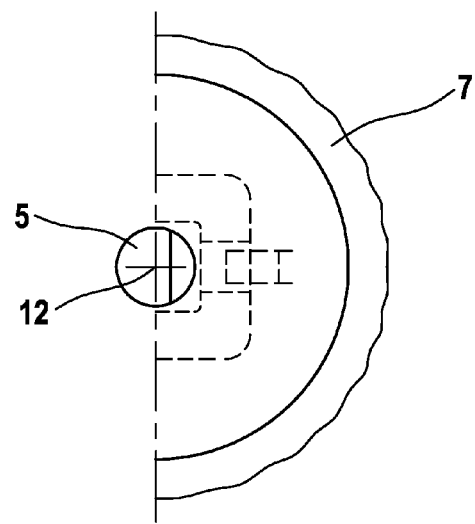

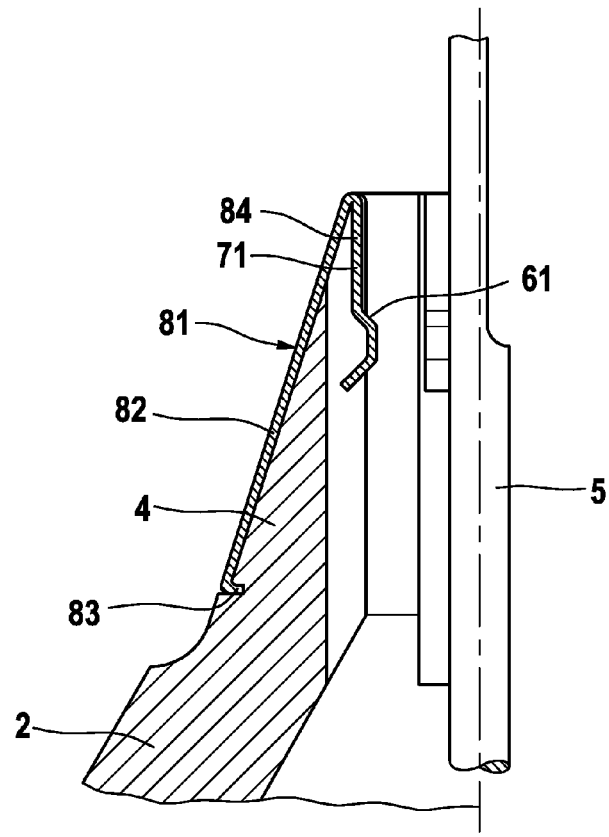
Fig. 10
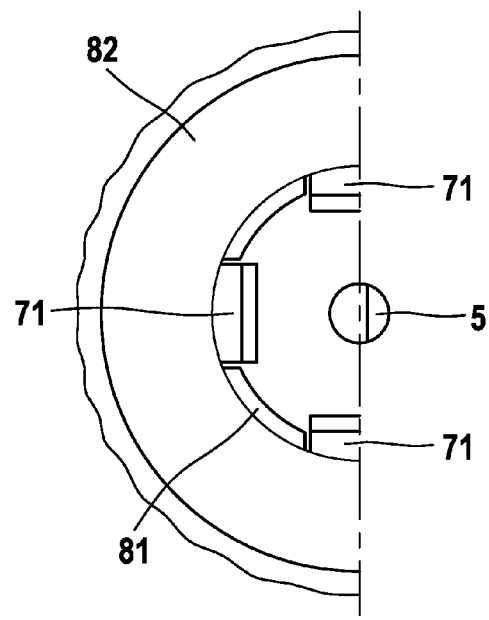

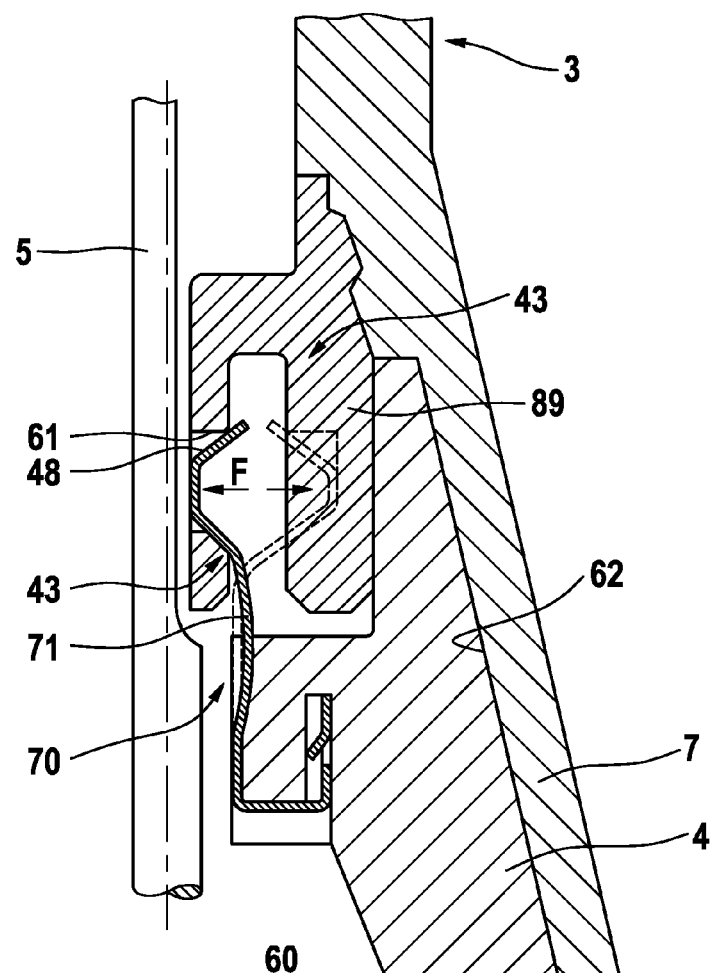
Fig. 16

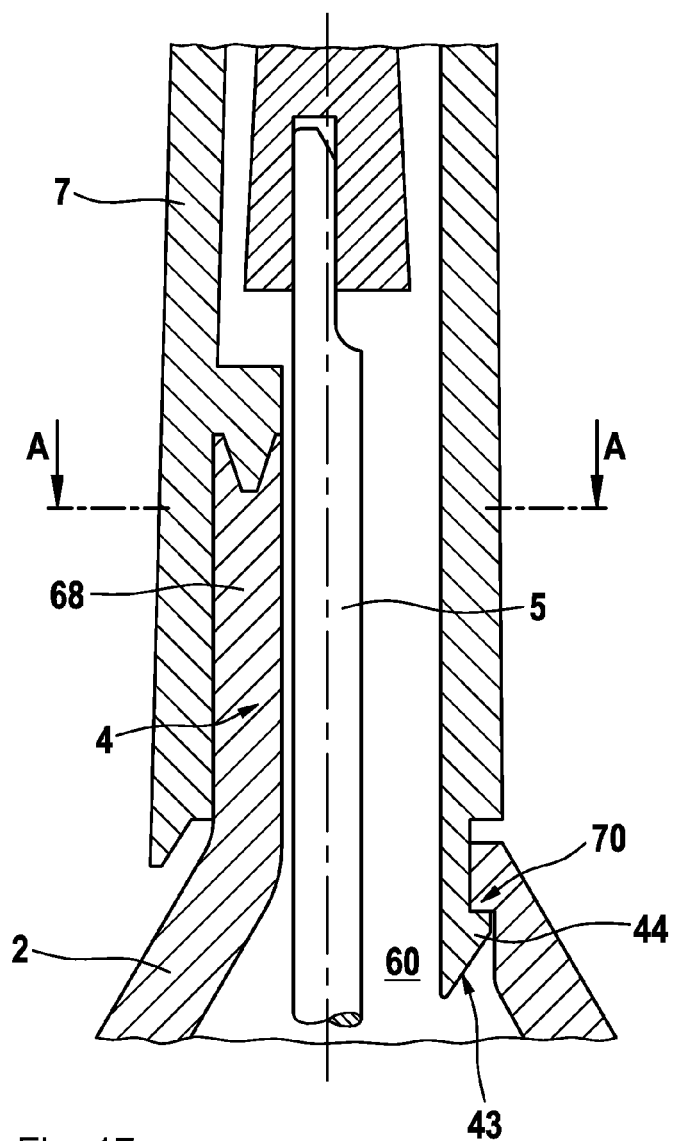
Fig. 17
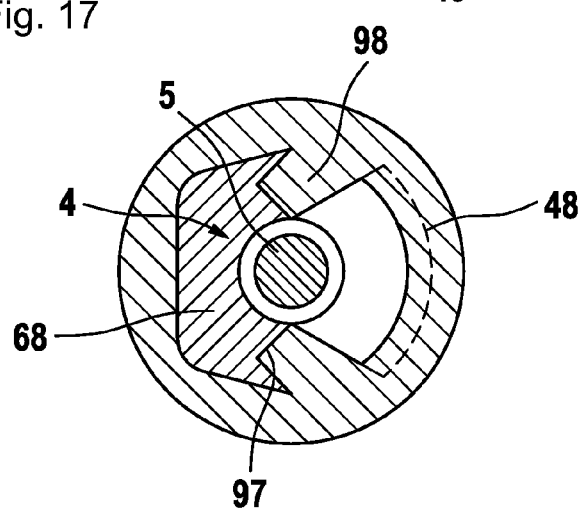

ELECTRIC TOOTHBRUSH

CROSS REFERENCE TO RELATED APPLICATIONS

This application claims the benefit of European Patent Convention Application No. 08011210.5, filed Jun. 20, 2008, the substance of which is incorporated by reference in its entirety herein.

FIELD OF THE INVENTION

The present disclosure is directed to an electric toothbrush. More particularly, the present disclosure is directed to an attachment part for an electric toothbrush, having a working head, a tubular connecting piece connected to the working head for connecting same to a neck of a toothbrush handle, and a drive shaft for driving the working head.

BACKGROUND OF THE INVENTION

Electric toothbrushes generally have removable and exchangeable attachment brushes, so that a common handle can be used by multiple family members, each having his or her own personal attachment brush, or so that in case of wear of the attachment brush only this attachment brush, and not the electric toothbrush as a whole, need be replaced. In the process, various forces must be transmitted by the coupling between the attachment brush and the handle, including in particular the cleaning forces, drive forces, axial forces, and radial forces that act on the attachment brush, or that act on the handle in the form of reaction forces. The coupling of the attachment brush to the handle neck is generally achieved in such a way that the radial forces are absorbed or dissipated in the handle neck and the axial forces are absorbed or dissipated in the drive shaft. For this purpose, the tubular connecting piece of the attachment brush is generally pushed onto the neck of the toothbrush, and the drive shaft provided in the brush tube of the attachment brush is coupled to the drive shaft that protrudes from the end of the handle neck. An example of such a system is described in EP 0500537 B1, according to which the handle neck, and, in a correspondingly complementary fashion, the tubular connecting piece, are provided with a cross-section that deviates from a circular shape in order to enable radial forces to be better absorbed. In order to enable transmission of the axial forces, the drive shaft in the brush tube can be pushed onto the drive shaft on the handle and secured there by a latching connection.

For such an electric toothbrush, WO 00/76420 A1 proposes that the axial fixing and also the fixing against rotation be achieved at the handle neck. For this purpose, sawtooth-shaped rubber lips are provided in the tubular connecting piece of the attachment brush, which lips can be pushed onto the handle neck, the shape of which deviates from a circular shape. In addition, latching tongues are provided on the tubular connecting piece that can be pushed over the outer circumferential surface of the handle neck and can be latched there; this is intended to achieve additional securing against a pulling off in the axial direction. However, the additional axial securing achieved by this latching device is limited due to the outer circumference of the handle neck becoming dirty, for example with toothpaste residue and the like. In addition, the neck of the toothbrush is sometimes grasped with the fingers, which can cause unintentional disengagement due to external pressure on the latching connection.

Furthermore, U.S. Pat. No. 6,836,917 proposes an electric toothbrush that has an L-shaped groove on the neck of the toothbrush, into which a pin provided on the push-on connecting piece of the attachment brush moves, such that the attachment brush can be secured by pushing it on and rotating it, in the style of a bayonet coupling. In addition, provision is made for an engaging of the drive shafts. However, radial forces can cause unintentional disengagement of the bayonet coupling if these forces are applied in the correct (so to speak) direction of rotation relative to the handle, thus making additional securing measures necessary.

In addition, from DE 102 09 320 A1 an electric toothbrush is known in which only a toothbrush head can be exchangeably latched to the handle; i.e., the toothbrush head does not have a drive shaft for driving same. Instead, a drive shaft on the handle must be threaded into the toothbrush head, which can sometimes pose problems and requires a particular drive movement of the drive shaft.

Thus, there is a need for an improved electric toothbrush, an improved attachment part, and/or an improved handle for such an electric toothbrush, which avoid the disadvantages of the prior art and improve upon the latter in an advantageous manner. In particular, an easy-to-operate coupling should be created between the attachment part and the handle that reliably absorbs the arising axial and radial forces, holds the attachment part firmly and with as little play as possible on the handle, and nonetheless permits easy disengagement of the coupling.

SUMMARY OF THE INVENTION

In one embodiment, an attachment part for an electric toothbrush is provided. The attachment part includes a brush head, a tubular connecting piece for connecting to the brush head to a neck of a handle of a toothbrush, and a drive shaft for driving the brush head, wherein the connecting piece has at least one interior latching element that is arranged such that it is suitable to move into the interior of the neck of the handle and to create a disengageable connection of the attachment part to the neck of the handle, the interior latching element being radially inwardly offset, with regard to the diameter thereof, relative to an internal cylindrical surface of the connecting piece, such that a gap remains between the exterior of the interior latching element and the internal cylindrical surface, the gap being suitably made such that a wall of the neck of the handle can be moved into it.

BRIEF DESCRIPTION OF THE DRAWINGS

The embodiments set forth in the drawings are illustrative in nature and not intended to limit the invention defined by the claims. The following detailed description of the illustrative embodiments can be understood when read in conjunction with the following drawings, where like structure is indicated with like reference numerals and in which:

FIG. 9 is a partial sectional view of another embodiment of an electric toothbrush in the area of the handle neck, according to which the interior latching means in the interior of the handle neck have a latching tongue in the form of a spring clip;

FIG. 10 is a partial sectional view of another embodiment of an electric toothbrush in the area of the handle neck according to which the interior latching means in the interior of the handle neck comprise a plurality of latching tongues that are integrally formed on a sheet-metal insert that is seated on the handle neck;

FIG. 16 is a partial sectional view of another embodiment of an electric toothbrush according to which the interior latching means provided in the handle neck comprise a latching tongue in the form of a spring clip, and the interior latching element of the attachment brush comprises an annular radial fitting element having a latching pocket; and FIG. 17 is a partial sectional view of another embodiment of an electric toothbrush, according to which half-shell-shaped coupling pieces are provided in each case on the tubular connecting piece of the attachment brush and on the handle neck, which coupling pieces can be placed onto one another with a precise fit.

DETAILED DESCRIPTION OF THE INVENTION

Figure 1:
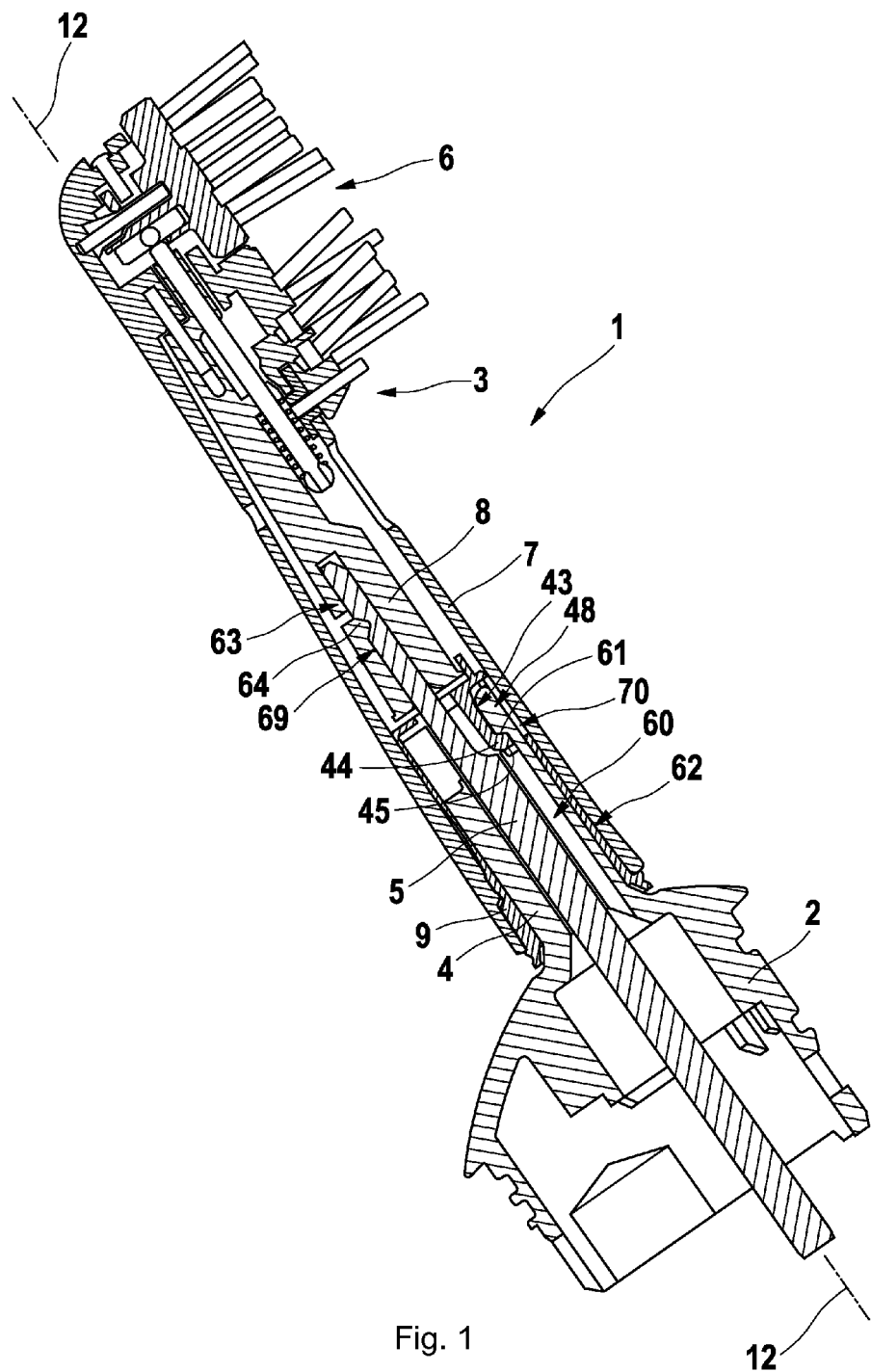
FIG. 1 is a partial sectional view of an electric toothbrush according to one embodiment having a handle and an attachment brush that can be pushed onto the handle neck, according to which the tubular connecting piece of the attachment brush has an interior latching element in the form of a latching hook that moves into the interior of the handle neck and latches there.

The following text sets forth a broad description of numerous different embodiments of the present disclosure. The description is to be construed as exemplary only and does not describe every possible embodiment since describing every possible embodiment would be impractical, if not impossible. It will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

According to the present disclosure, the radial forces and axial forces acting between the attachment part and the handle should act on the handle neck, and that a connection provided for this purpose between the tubular connecting piece of the attachment part and the handle neck be relocated to the interior of the handle neck. The tubular connecting piece of the attachment part has an element for the form-closed and/or force-closed connecting of the attachment part to the handle.

In one embodiment, the tubular connecting piece of the attachment part has an interior latching element that is formed and arranged in such a way that when the attachment part is placed onto the handle neck, the latching element moves into the interior of the handle neck and latches on an inner contour of the handle neck. Correspondingly, the toothbrush handle is distinguished in that the handle neck has internally arranged interior latching means for engagement with the interior latching element of the attachment part which moves into the interior of the handle neck. Owing to the latching connection in the interior of the handle neck, axial forces can be reliably absorbed, which also permits a special design of the interface of the drive shafts of the handle and the attachment part, because this interface is no longer forced to absorb pull-off forces. A secure engaging is possible in this case with a low risk of the latching surfaces becoming dirty and without adverse effects due to external pressure on the toothbrush handle, and the latching connection is able to absorb both axial forces and radial forces. In another embodiment, the tubular connecting piece of the attachment part has an internal clamping element that is formed and arranged in such a way that when the attachment part is placed onto the handle neck it moves into the interior of the handle neck and clamps onto an inner contour of the handle neck. The handle of the toothbrush is correspondingly distinguished in that the handle neck has an internally arranged contour for clamping with the internal clamping element of the attachment part that moves into the interior of the handle neck. In another embodiment, the tubular connecting piece of the attachment part has an internal latching and clamping element that is formed and arranged in such a way that when the attachment part is placed onto the handle neck it moves into the interior of the handle neck and locks and clamps on an internal contour of the handle neck. The toothbrush handle is correspondingly distinguished in that the handle neck has an internally arranged contour for engaging and clamping with the internal latching and clamping element of the attachment part.

The invention is described below using form-closed coupling means between the electric toothbrush and the handle thereof as an example. However, it is to be understood that the coupling between the electric toothbrush and the handle thereof can be implemented on the basis of a force-closed connection as well.

The internal latching means, arranged in the interior of the handle neck, between the tubular connecting piece of the attachment part and the handle neck can be designed in various ways. Advantageously, the interior latching element of the attachment part can have a latching tongue that extends toward the end face of the connecting piece, for example projecting toward the handle of the toothbrush, the tongue having a latching contour the shape of which is matched to the inner contour of the handle neck, which contour can for example be formed as a latching recess or as a latching projection. In particular, the latching tongue can form a latching hook that has on the end thereof a hook-shaped latching projection that can lock on a latching contour, formed complementary thereto, inside the handle neck. The orientation of the latching contour on the latching tongue can be selected varyingly. For example, an orientation of the latching contour in the circumferential direction may be provided, such that a latching can take place by the latching tongue springing away in the circumferential direction when the attachment part is pushed on axially. In another embodiment, however, the latching contour is provided on the radially outward-facing side of the latching tongue.

The latching tongue advantageously forms a spring clip that extends approximately in the longitudinal direction of the tubular connecting piece of the attachment part and is formed so as to be elastically deformable transverse to the longitudinal direction. In conjunction with the above-described arrangement of the latching contour on the outer side of the latching tongue, in this way a latching can easily take place in that when the attachment part is axially pushed onto the handle neck, the latching tongue at first springs away in the radial direction until it has reached the complementary latching contour in the interior of the handle neck, so that in the fully pushed-on position it can then lock by springing back.

Particularly simple operation can be achieved through an undercut design (relative to the longitudinal direction of the tubular connecting piece) of the interior latching element. The attachment part need merely be pushed on axially, approximately parallel to the longitudinal direction of the tubular connecting piece or handle neck, thereby enabling the latching device to lock. Conversely, the latching connection can be disengaged by axially pulling off the attachment brush.

In order on the one hand to enable a firm latching connection that can absorb high axial forces and on the other hand to enable an easy disengagement of the latching connection when the attachment brush is pulled off, the interior latching element of the attachment part can have assigned thereto an unlatching bevel that is inclined at an acute angle to the longitudinal direction of the tubular connecting piece, for example, in the form of a wedge surface, via which the engaging latching contours can be disengaged from one another. The latching contours themselves can at the same time be formed in such a way in this case that they can also withstand higher forces, for example, in the form of latching surfaces that run transverse to the longitudinal direction.

Despite the internal latching connection of the attachment part on the handle neck, it is advantageous to provide that the attachment part be pushed onto the outer circumferential surface of the handle neck. For this purpose, there is provided on the tubular connecting piece of the attachment part an outer coupling piece for placement onto the outside of the handle neck. The outer coupling piece forms a surrounding piece that surrounds the handle neck on the outside thereof. In this way, a tilt-proof and also rotationally fixed connection can be created between the attachment part and the toothbrush handle, which can also transmit larger brushing forces.

The outer coupling piece in this case can comprise an internal cylindrical surface piece that advantageously forms a form-closed mating surface, relative to which the interior latching element of the attachment part is radially inwardly set back, or is separated by a gap into which a wall of the handle neck can move when the attachment part is pushed on. The wall of the handle neck is thus embraced from both sides, so to speak. The outer coupling piece of the connecting piece is moved over the outer circumferential surface of the handle neck, while the interior latching element of the connecting piece moves into the handle neck on an inner side thereof.

On the handle, interior latching means can be provided that are formed in various ways. If, as described above, a spring-type latching tongue is provided on the attachment part in the form of a spring clip, the interior latching means can be formed on the handle in the form of a latching contour that is provided in stationary fashion on the handle neck, which contour is advantageously undercut in the longitudinal direction of the handle and is suitably adapted in the shape thereof to the latching contour of the latching tongue. In particular, a radially inwardly protruding latching projection can be integrally formed on the internal cylindrical surface of the handle neck.

Alternatively, or in addition, the interior latching means in the interior of the handle neck can also have a latching tongue, in one example, in the form of an elastic spring clip that extends substantially parallel to the longitudinal direction of the handle neck and is formed so as to be elastically deformable transverse to the longitudinal direction. When the attachment part is pushed on in the axial direction, this latching tongue can slide over the interior latching element of the attachment part with elastic deformation until it locks in the fully pushed-on position by springing back. In one embodiment, such a latching tongue in the interior of the handle neck can be formed in such a way that it can spring away in the radial direction and can latch through corresponding springing back in the radial direction.

In further embodiments, latching means can be provided in a known manner on the shaft coupling pieces of the drive shaft on the handle and the drive shaft of the attachment part, by means of which the drive shafts can be latched to one another. The latching means in this case are advantageously formed such that they can be latched together and disengaged by axially pushing the drive shafts or shaft coupling pieces onto one another. For this purpose there can be provided on a shaft coupling piece a latching clip having a suitable latching contour, extending in the longitudinal direction of the shaft, that is capable of latching in a complementary latching contour on the other shaft coupling piece.

Alternatively or in addition to such a latching of the shaft coupling pieces, the shaft coupling pieces can however also have a conical fit, i.e., in particular mutually complementary conical clamping mating surfaces can be provided on the shaft coupling pieces that can achieve a play-free fit by axially pushing the shaft coupling pieces onto one another. Due to the engagement of the attachment part on the handle neck, axial forces need not necessarily be transmitted via the drive shaft coupling, and therefore the bevel angle of the conical or inclined clamping mating surfaces can also be made larger, in particular large enough that an automatic engagement no longer occurs. Advantageously, bevel angles of greater than approximately 7 degrees to the longitudinal axis of the drive shaft can be provided on the clamping mating surfaces. In this way, a play-free coupling can be achieved even when short axial coupling paths are used, and the axial forces can easily be absorbed via the latching connection on the handle neck, or, optionally also via a latching connection additionally provided on the shaft coupling pieces.

The drive shaft on the attachment part and/or on the handle, or the shaft coupling piece respectively coupled thereto, can be mounted so as to be axially movable. Advantageously, the respective drive shaft and/or the shaft coupling piece connected thereto has assigned to it a biasing device by means of which the shaft coupling piece on the attachment part is biased toward the handle, or, alternatively, the shaft coupling piece on the handle is biased toward the attachment part. In particular, the biasing device can include a spring device that is provided between the shaft coupling piece and the associated drive shaft. In particular, the shaft coupling piece can be supported on the drive shaft via a compression spring, such that the shaft coupling piece is, so to speak, slightly compressed when the attachment part and handle are brought together. In this way, a play-free coupling of the drive shafts of the attachment part and the handle can be achieved. The biasing is particularly advantageous in conjunction with conical clamping mating surfaces and in conjunction with the above-described internal engagement of the attachment part on the handle neck, but can also be used independently thereof to achieve a play-free, firm, and easily disengageable coupling of the two drive shafts.

The outer coupling piece of the tubular connecting piece can form a push-on ring that can be pushed onto the neck of the toothbrush or the external cylindrical surface thereof; the push-on ring can be formed in a closed manner. The push-on ring can be designed conical in shape and can be matched to a conical external cylindrical surface of the handle neck. However, it is also possible to provide a shell-shaped coupling piece on the tubular connecting piece of the attachment part, the coupling piece being capable of being placed onto a half-shell-shaped coupling piece on the handle neck. The two shell-shaped or half-shell-shaped coupling pieces complete each other, to form a complete handle neck or connecting piece, capable in particular of reliably absorbing forces in the circumferential direction that would be caused by a twisting of the attachment part on the handle. In addition, a design having a particularly small diameter can be achieved.

On the handle neck, there can be provided a coupling device having a coupling piece that is movable in the longitudinal direction of the handle in order to bring about a form-closed and/or frictional locking with the connecting piece of the attachment brush. The coupling piece is pressed away axially from the grip portion of the handle of the toothbrush by a spring element, such that when the attachment part is not attached, the coupling piece is arranged in a defined position relative to the handle, in which the attachment part can be attached in an unhindered manner.

The coupling device on the handle neck operates with an axial movement in the longitudinal direction of the handle and with a movement transverse to the longitudinal direction of the handle. The axial movement in the longitudinal direction of the handle brings about the actuation of the coupling device, and the transverse movement brings about the locking. The handle of the toothbrush is distinguished in that the coupling device thereof has a coupling piece that can be moved axially in the longitudinal direction of the handle, the coupling piece being mounted and/or formed in such a way that an axial movement of the coupling piece produces a transverse movement of the engagement part of the coupling device, transverse to the longitudinal direction of the handle.

The axial actuating movement can be produced by the attachment part when it is pushed onto or pulled off from the handle neck. The pushing on or pulling off of the attachment part can be used to produce a locking movement or unlocking movement, oriented transverse to the pushing-on or pulling-off movement, of the coupling device on the handle. According to another aspect, the attachment part is distinguished in that the coupling piece thereof has, on an internal cylindrical surface, an outwardly oriented recess into which the engagement part of the coupling piece on the handle can be moved, as well as an impact surface for the axial recoil of the coupling piece on the handle when the connecting piece is placed onto the handle neck. The impact surface on the coupling piece of the attachment part is matched, with regard to the shape and position thereof, to the coupling piece on the handle in such a way that the impact surface catches the coupling piece of the toothbrush handle when the attachment part and the toothbrush handle are placed together, and slides back axially relative to the grip portion of the handle of the toothbrush, such that the locking is brought about so to speak automatically when the attachment part is attached.

In order to bring about the transverse movement of the engagement part of the coupling device on the handle, which causes the engagement, there can be provided between the handle neck and the coupling piece of the handle of the toothbrush a spreading mechanism by which the above engagement part of the coupling device on the handle is spread outward, transverse to the longitudinal direction of the handle, when there is an axial movement of the coupling piece toward the body of the handle. It is the coupling piece itself in this case that is spread outward by the spreading mechanism when there is a corresponding axial movement, and the engagement part can therefore be provided directly on the coupling piece, preferably integrally formed in one piece thereon.

The coupling device can have assigned thereto a control device that operates mechanically and that controls the drive of the toothbrush according to the position of the coupling device. In particular, the control device can have inhibiting means that block, switch off, retard or brake the drive of the toothbrush when the engagement section of the coupling device is not in the latching position thereof. This can prevent the toothbrush drive from moving when the attachment brush is not correctly seated on the handle; in this way, in particular a risk of injury due to a rotating drive shaft can be prevented. The inhibiting means can in principle be formed in various ways, for example, control-technology or software based. Alternatively, or in addition, a mechanical design of the inhibiting means can be provided, wherein the inhibiting means can comprise an engagement surface on the coupling piece that, in the non-locked position of the coupling piece, can move into engagement with a drive shaft of the handle, and in particular can be pressed against the drive shaft. In particular, the inhibiting means can comprise flattened parts on the drive shaft and on the coupling piece on the handle, such which flattened parts can be brought into contact with each other. If the flattened part of the coupling piece presses against a corresponding flattened part of the drive shaft, the drive shaft can no longer rotate. The flattened parts may be arranged on the outer surface.

The inhibiting means can work together in this case with an electronic switch-off device for the drive motor. In particular, the control device can have an electronic switch-off device that switches off the drive motor when the drive shaft is being retarded. As soon as the electronic switch-off device notices that the drive shaft of the toothbrush cannot move freely, the drive motor is switched off in order to protect the motor and in particular also the batteries. The detection of the inhibiting situation of the drive shaft can take place in various ways. For example, a position sensor could be provided, for example a switch that detects the position of the above-mentioned coupling piece. If same is in the inhibiting position thereof, the drive motor is switched off. However, the switching off of the motor can also take place on the basis of the power consumption thereof. In particular, the above-mentioned switch-off device can comprise detection means for detecting the motor current and can switch off the drive motor when the motor current exceeds a predetermined motor current level. This occurs when the drive shaft is retarded or braked.

Through such a mechanical inhibiting of the drive shaft of the handle of the toothbrush when the attachment part is removed, in conjunction with an electronic switch-off device of the drive motor, a very simple travel lock with battery protection can be achieved. It is necessary merely to remove the attachment part from the handle of the toothbrush in order to prevent the handle of the toothbrush from being switched on unintentionally. Even if same is for example placed loosely in a suitcase, the rechargeable battery of the toothbrush cannot undergo an undesired discharge.

In order to ensure placement and coupling of the attachment part on the handle neck of the toothbrush with a precise fit even when there is dirt on the mating surfaces, there can be provided on the handle neck of the toothbrush, and/or on the connecting piece of the attachment part, dirt-catching recesses into which specks of dust, crumbs, or the like can disappear, when the two parts of the toothbrush are placed onto one another, such that they do not hinder the coupling process. These dirt catching recesses can be provided in particular on the cylindrical or conical mating surfaces of the handle neck and the attachment part, in particular on the external cylindrical surface of the handle neck and on the internal cylindrical surface of the connecting piece of the attachment part. Alternatively, or in addition, such dirt catching recesses can also be provided on the inhibiting piece of the handle of the toothbrush and/or of the attachment part and/or on the engagement parts provided thereon, such that the coupling process is not hindered. For example, it can be provided that the outer surface of the spreadable inhibiting piece and/or the inner surface, which can be brought into engagement therewith, of the attachment part be provided with such dirt catching recesses, such that the spreading of the inhibiting piece is not hindered.

The dirt catching recesses can be formed in various ways, for example, in the form of a surface fluting, in particular in the form of a longitudinal fluting having catching recesses that are substantially groove-shaped and that run in the longitudinal direction of the toothbrush.

Turning to the Figures, toothbrush 1 shown in the Figures comprises a handle 2 and an attachment part connected thereto in the form of an attachment brush 3. Handle 2, shown only partially, comprises in a known manner a housing that accommodates a drive motor and an energy supply device such as a rechargeable battery, and on which there is provided an actuating switch for switching the drive on and off. On the end face, shown in FIGS. 1 to 3, of handle 2, the housing of handle 2 forms a handle neck 4 that, in the depicted embodiment (viewed as a whole), is formed as a connecting piece that protrudes from the end face and is truncated or frustum-shaped and is substantially cylindrical or conical, and that can taper slightly in conical fashion towards the free end thereof. A drive shaft 5, which can for example be driven in a rotationally oscillating fashion, emerges from the end face of handle neck 4.

Attachment brush 3 comprises a working head 6 having a field of bristles (not shown in more detail) that can be driven in rotationally oscillating fashion about a bristle field axis that points approximately in the longitudinal direction of the bristles. The working head 6 is borne by a connecting piece 7 that has an overall tubular shape and that can be pushed onto neck 4 of toothbrush handle 2. Inside the tubular connecting piece 7, attachment brush 3 has a push-on shaft 8 that can be coupled in rotationally integral fashion to drive shaft 5 on the handle.

In order to fasten attachment brush 3 on handle 2, in tubular connecting piece 7 there is provided a coupling insert 9 in the form of a coupling sleeve or coupling ring that is arranged so as to be axially fixedly seated in tubular connecting piece 7. The coupling insert 9 is overall cylindrical or slightly conical in shape, such that coupling insert 9 can be axially pushed onto neck 4 of the handle with an overall precise fit, such that a play-free fastening with a precise fit of the attachment brush on handle 2 can be achieved.

The coupling insert 9 forms with the internal cylindrical surface of the tubular connecting piece 7, an outer coupling piece 62 that can be pushed onto outer circumferential surface of neck 4 of the handle with a precise fit, and surrounds this neck. Outer coupling piece 62 thus forms a surrounding part that fixes attachment brush 3 on neck 4 of the handle in a tilt-proof manner. In order to prevent neck 4 of the handle, which is formed with a slightly conical shape, from sliding down axially, in interior 60 of neck 4 of the handle there is provided a latching connection of attachment brush 3 to neck 4 of the handle. In the depicted specific embodiment, for this purpose attachment brush 3 comprises an interior latching element 43 that is provided inside tubular connecting piece 7, the interior latching element being integrally formed on coupling insert 9 in the depicted specific embodiment; however, in another embodiment this interior latching element may also be provided directly on the wall of tubular connecting piece 7.

As shown in FIG. 1, interior latching element 43 is formed as a latching tongue in the form of a latching hook 44 the longitudinal extension of which runs substantially parallel to longitudinal direction 12 of attachment brush 3, and that protrudes from the floor of coupling insert 9 (which is formed as a blind hole) toward the end face of connecting piece 7, or toward handle 2. On the protruding end of latching element 43, latching hook 44 has a latching contour 61 in the form of a latching projection that protrudes radially outward from the outside of latching hook 44 and is formed so as to be undercut in the longitudinal direction of attachment brush 3. With regard to the diameter thereof, interior latching element 43 is offset radially inward relative to the internal cylindrical surface of coupling insert 9, such that between the outside of interior latching element 43 and the internal cylindrical surface of coupling insert 9 there remains a gap into which the wall of neck 4 of the handle can move.

Latching contour 61 of interior latching element 43 locks with interior latching means 70 in interior 60 of neck 4 of the handle. Latching means 70 comprises a latching contour 48 in the form of a latching projection that protrudes radially inward from the internal cylindrical surface of the wall of neck 4 of the handle and that is formed so as to be undercut relative to longitudinal direction 12. Here, latching contour 48 is integrally formed in one piece on the wall of neck 4 of the handle.

As FIG. 1 shows, undercut latching contours 48 and 61 of interior latching means 70 or of latching hook 44 are each inclined at an acute angle to longitudinal direction 12, such that the latching connection can be disengaged by forcefully pulling on attachment brush 3. Moreover, the inclined position of the latching contours ensures a play-free coupling, because in this way an axial force can be produced when latching hook 44 presses elastically against the complementary latching contour on neck 4 of the handle. The latching hook 44 is advantageously formed as a spring clip that can spring away transverse to longitudinal direction 12, in particular in the radial direction.

In this way, the following function results: in order to couple attachment brush 3 to handle 2, it is necessary merely to axially push attachment brush 3, with the tubular connecting piece 7 thereof, onto neck 2 of the handle. In this way, outer coupling piece 62 of tubular connecting piece 7 slides over the external cylindrical surface of neck 4 of the handle. Inside neck 4 of the handle, latching hook 44 slides over latching contour 48 on the handle, elastically bending away in the process. At the same time, shaft coupling piece 63 of drive shaft 8 of attachment brush 3 is threaded onto shaft coupling piece 69 of drive shaft 5 of handle 2.

When the fully pushed-on position is reached, latching hook 44 springs back radially, causing latching contours 48 and 61 to move into engagement with one another. At the same time, drive shaft 5 locks with drive shaft 8 provided in the attachment part. For this purpose, the two shaft coupling pieces 63 and 69 that move into engagement with one another comprise a latching connection that, in FIG. 1, comprise latching means 64 in the form of an elastic latching tongue that can spring away radially to the longitudinal direction of the drive shaft and locks by radially springing back.

Neck 4 of the handle can have various cross-sectional shapes. If it is formed cylindrically or conically, the latching connection in interior 60 of neck 4 of the handle can secure the attachment brush against rotation. This can easily be accomplished in that latching hook 44 not only locks in the axial direction, but is also guided on neck 4 of the handle in the circumferential direction, in that latching hook 44 moves into a groove-shaped pocket or similar guide means on neck 4 of the handle. Alternatively, or in addition, neck 4 of the handle and, complementary thereto, coupling insert 9 can have a cross-section that is not round and that acts to dissipate rotational forces. Alternatively or in addition, an additional securing means against rotation can be provided in the side opposite interior latching element 63, for example, in the form of a pin that extends axially into the toothbrush neck.

Figure 2:
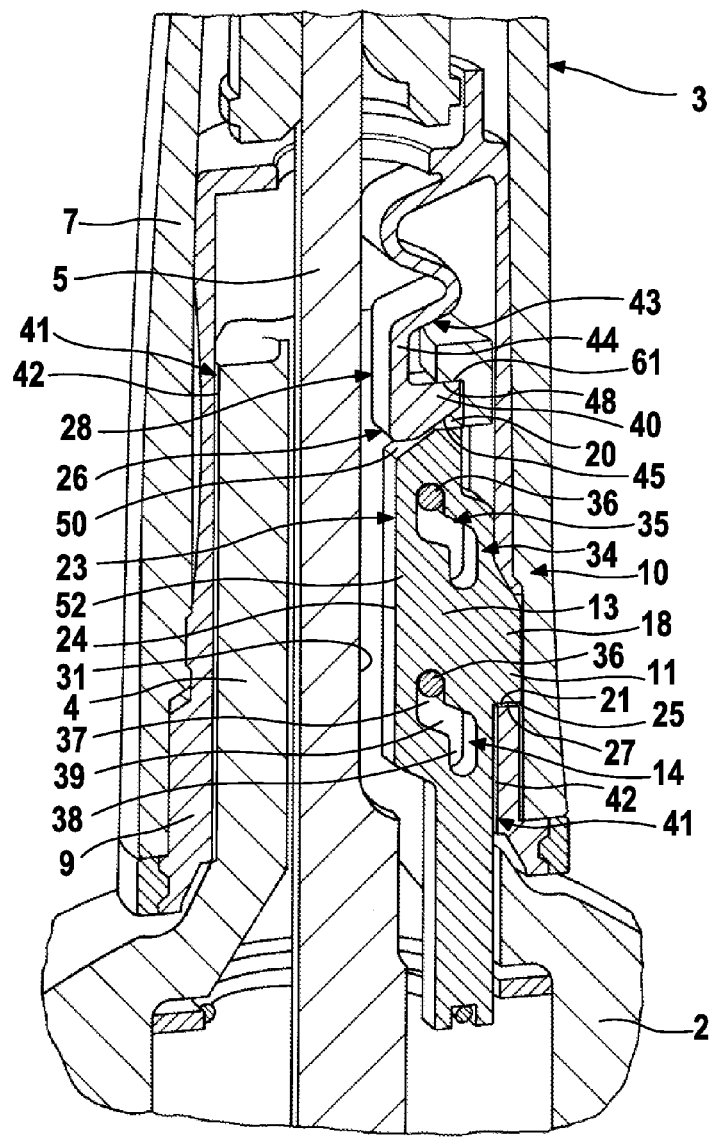
FIG. 2 is a partial sectional view of another embodiment of an electric toothbrush according to which the latching hook comprises a spring clip that is curved with a meander shape, and according to which there is provided in the handle of the toothbrush a spreadable coupling/inhibiting piece for locking the attachment brush and inhibiting the drive shaft when the attachment part is removed.

FIG. 2 shows a basically similar design of toothbrush 1 that differs from the embodiment shown in FIG. 1 substantially through the design of interior latching element 43, and through the provision of a spreadable coupling/inhibiting piece 13 inside neck 4 of the handle. As FIG. 2 shows, there is provided on neck 4 of toothbrush handle 2 a rib-shaped and/or approximately half-shell-shaped coupling and inhibiting piece 13 that on the one hand forms a inhibiting means 23 for blocking drive shaft 5 and the same time forms a coupling piece of a coupling device 10 on the handle that can be brought into latching engagement with coupling insert 9 on the attachment brush. Frustum-shaped neck 4 of the handle is so to speak bifurcated, into a body part that is connected rigidly to the housing of the handle and that forms the actual neck 4 of the handle, and movably mounted inhibiting and coupling piece 13 that, in the initial position in which drive shaft 5 is blocked, substantially continues the contour of neck 4 of the handle and together therewith forms the connecting frustum onto which tubular connecting piece 7 can be pushed. In particular, in the initial position inhibiting and coupling piece 13 is seated with a flattened part on a likewise flattened section of drive shaft 5 in order to impede this drive shaft.

As FIG. 2 shows, a spreading mechanism 14 for spreading inhibiting piece 13 can have a sliding guide in the form of a sliding block guide 34. In the specific embodiment depicted in FIG. 2, inhibiting and coupling piece 13 comprises a sliding block guide 35 in the form of two guide grooves, having the shape of longitudinal grooves and angled off in a step-like manner, in which two guide pins 36 engage the diameter of which corresponds approximately to the width of the guide grooves, in order to achieve an substantially play-free sliding guidance of inhibiting piece 13. Instead of the two guide grooves shown in FIG. 2, optionally it could also be possible to provide only one guide groove, optionally in combination with a further support of inhibiting piece 13, such that during the spreading this inhibiting piece would additionally experience a pivoting movement.

Guide sliding block 35 can comprise guide segments 37, 38, and 39 that are inclined at different angles to longitudinal direction 12 of the handle, so that the stroke or spread movement of inhibiting piece 13 goes through a plurality of phases. In one embodiment, a more steeply inclined middle guide segment 39 is provided that goes over into less strongly inclined guide end segments 37 and 38. Guide end segments 37 and 38 are advantageously oriented substantially parallel to longitudinal direction 12 of the handle, such that when guide pins 36 are arranged in the area of these guide end segments 37 and 38, no stroke movement of inhibiting piece 13 takes place, and the inhibiting piece is held at the respective degree of spreading without axial forces. Optionally, guide end segments 37 and 38 can also be inclined slightly in the opposite direction (relative to the inclination of center guide segment 39), such that a slight overtravel occurs when the end positions are approached.

The inclination of center guide segment 39 is matched to the properties of coupling device 10, in particular the length of the push-on movement and the diameter of the neck of the handle, as well as the size of the flattened part of drive shaft 5. In the embodiment shown in FIG. 2, an angle of inclination in the range from about 45° to about 80° is provided. In this way, the following functioning results: when the attachment brush 3 is pushed onto neck 4 of the handle, at first inhibiting and coupling piece 13 remains in the moved-in, non-latching end position thereof. Coupling insert 9 has in the run-in area thereof, up to recess 25, an inner clearance that, regarded radially, is greater than the radial dimension of latching nose 18 of inhibiting piece 13.

In this way, attachment brush 3 can be pushed over inhibiting and coupling piece 13 until latching nose 18 of the attachment brush comes to rest in the area of recess 25. However, when attachment brush 3 is pushed on further, inhibiting and coupling piece 13 impacts, with an impact surface 20 provided on the end face thereof that extends transverse to longitudinal direction 12 of the handle, against impact surface 26 on actuating projection 28 of coupling insert 9. In this way, inhibiting and coupling piece 13 is axially carried along as attachment brush 3 is further pushed on, causing inhibiting piece 13 to move in slide block guide 34. Via inclined center guide segment 39, inhibiting piece 13 is radially pressed outward in this arrangement, such that the latching nose 18 thereof moves into window-type recess 25 of attachment brush 3.

As FIG. 2 shows, actuating projection 28 of attachment brush 3, which carries along inhibiting and coupling piece 13, is here formed in the form of a spring clip that, in the fully pushed-on position, latches on neck 4 of the handle, and to this extent forms a latching device or the interior latching element 43. In particular, latching hook 44, when it moves into the interior of neck 4 of the handle, can there first radially spring away and slide over a neck contour on the handle. When the end position is reached, latching hook 44 can lock into an undercut recess and spring back. In the depicted embodiment, here latching hook 44 is provided with a radially protruding latching nose that moves into a latching recess provided on neck 4 of the handle. This achieves an additional retention of attachment brush 3 in the pushed-on position.

Still referring to FIG. 2, when attachment brush 3 is pulled off, inhibiting piece 13 moves back, in the opposite direction, to the inner position thereof. In this arrangement, an entraining surface 27 provided on coupling insert 9 carries along entraining surface 21 provided on inhibiting and coupling piece 13, and thus carries inhibiting piece 13 along in the axial direction. At the same time, actuating projection 28 is unlocked via a bevel 45 on the latching nose 40 thereof. As the pulling off continues, inhibiting and coupling piece 13 moves radially inward in slide block guide 34 far enough that the inner contour of attachment brush 3 can be pulled over latching nose 18 of inhibiting piece 13; cf. FIG. 2. At the same time, inner flattened part 24 of inhibiting and coupling piece 13 is seated against flattened part 31 of drive shaft 5, which is thereby blocked.

Dirt catching recesses 41 are provided on the mating surfaces of the toothbrush handle and the attachment part, into which specks of dust, dirt particles, and the like can fall into, such that they do not hinder the coupling process. In particular, flutings 24 in the shape of longitudinal grooves can be provided as dirt catching recesses 42 on the outer surface of inhibiting piece 13 and/or on the outer surface of neck 4 of the handle.

Figure 3:
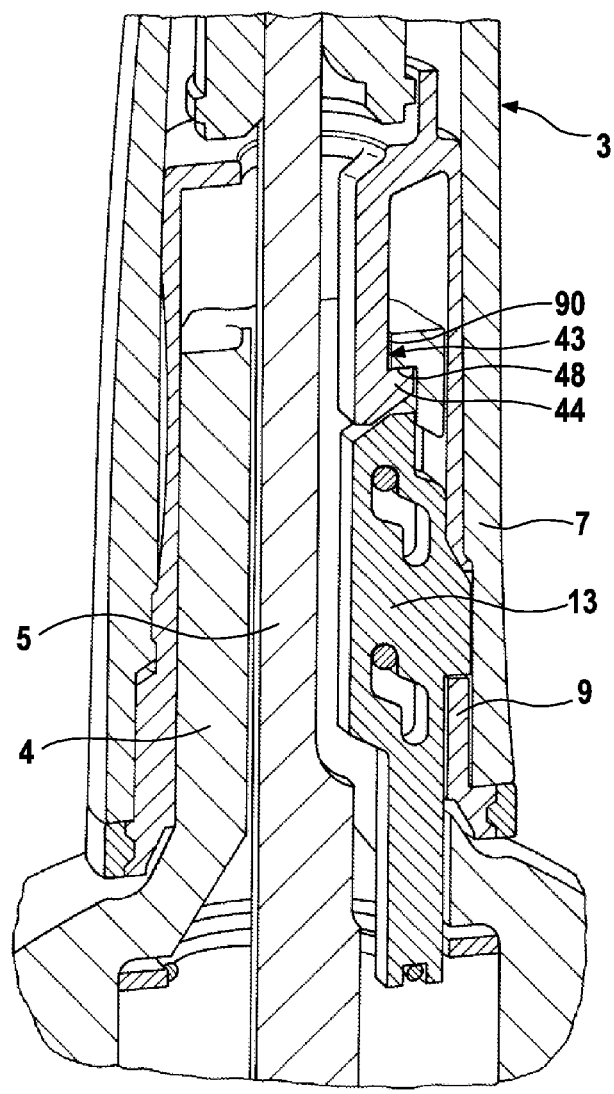
FIG. 3 is a partial sectional view of another embodiment of an electric toothbrush according to which a latching hook locks in the interior of the handle neck, and a spreadable coupling/inhibiting piece, via which the latching connection can be disengaged, is provided in the handle neck.

FIG. 3 shows a fundamentally similar embodiment. However, here a latching hook 44 is not curved with a meander shape, as in the embodiment according to FIG. 2; rather, it is formed in the form of an arm that runs substantially straight, or a straight latching tongue the outer side 90 of which, in the locked position, stands radially against the inner surface of latching contour 48 on the handle. Latching contour 48 can here be formed in the form of a pocket into which the latching projection of latching hook 44 springs, such that the latching hook is also guided in the circumferential direction in order to transmit circumferential forces. In other respects, the embodiment according to FIG. 3 corresponds substantially to that according to FIG. 2, and reference is therefore made to the further description thereof.

Figure 4:
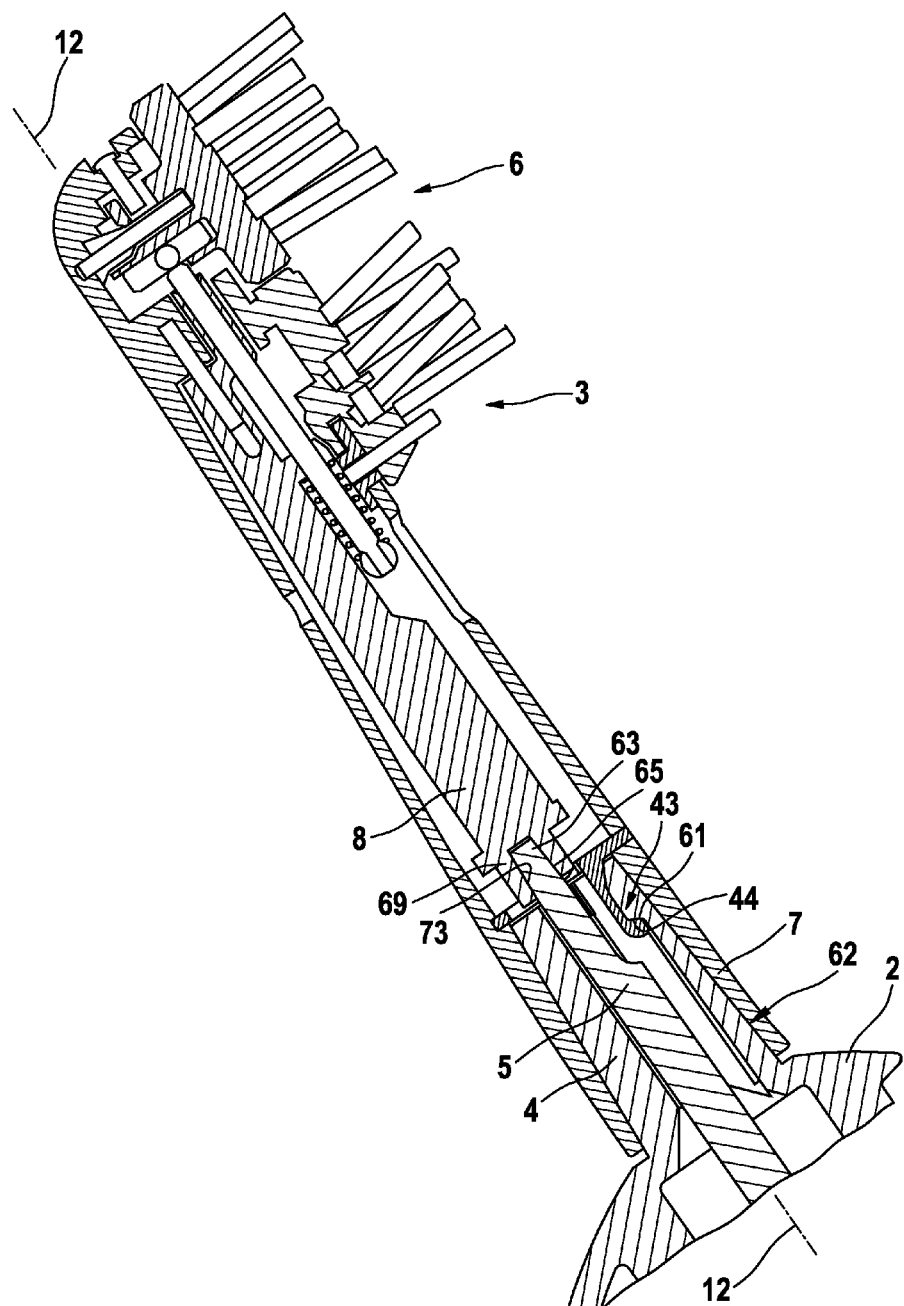
FIG. 4 is a partial sectional view of another embodiment of an electric toothbrush according to which the drive shafts in the attachment brush and in the handle are connected to one another via a conical press-fit surface pair, and the handle neck has an external cylindrical surface that tapers in a conical fashion.

FIG. 4 shows another embodiment of toothbrush 1. In this embodiment, interior latching element 43, which again is formed as latching hook 44 in a manner similar to the preceding Figures, is not provided on a separate coupling insert 9, but rather is provided directly on the wall of tubular connecting piece 7, in particular being integrally formed thereon in one piece. However, a design having a coupling insert 9 in a manner similar to the above-described Figures would be possible here as well, of course. Differences from the preceding Figures, however, include the design of outer coupling piece 62 and the contour, complementary thereto, of neck 4 of the handle, as well as the design of shaft coupling pieces 63 and 69 of drive shafts 5 and 8. The external cylindrical surface of neck 4 of the handle is conical, in particular tapered, such that the angle of inclination relative to longitudinal direction 12 can be greater than approximately 7 degrees, which inherently prevents the possibility of an automatic engagement. This enables a play-free fit even given short push-on paths. The axial securing of attachment brush 3 on neck 4 of the handle is brought about by the engagement in the interior of neck 4 of the handle in the manner described above.

Likewise, the interface of drive shafts 5 and 8 is conical, mutually complementary clamping mating surfaces 65 and 73 being provided on shaft coupling pieces 63 and 69 that can be plugged together; the angles of inclination of these mating surfaces relative to longitudinal direction 12 of attachment brush 3 can also be greater than approximately 7 degrees. In this way, a play-free connection with a precise fit between drive shafts 5 and 9 can be achieved by axial pushing together even given short actuating paths. Such a conical or tapered realization of shaft coupling pieces 63 and 69 can be particularly advantageous in conjunction with an axial biasing of drive shaft 8 and/or 5, as is shown in FIGS. 6 and 7.

Figure 6:
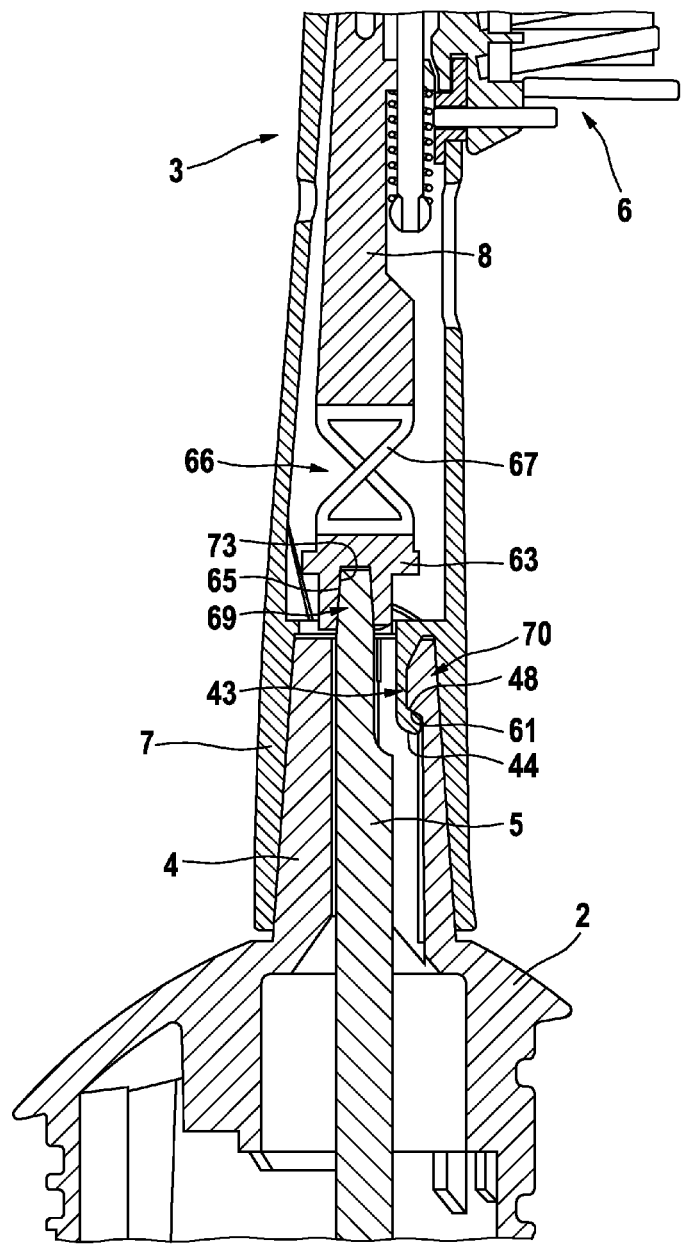
FIG. 6 is a partial sectional view of another embodiment of an electric toothbrush according to which a shaft coupling piece of the drive shaft in the attachment brush is movable in the axial direction and is biased by a spring device in order to achieve a play-free seating of a conical clamping fit surface pair between the drive shafts.

With regard to the engagement of tubular connecting piece 7 to neck 4 of the handle, the embodiment according to FIG. 6 is implemented in a manner similar to the preceding embodiments and reference is therefore made to the description thereof. In particular, as is shown in FIG. 6, on connecting piece 7 there is provided an interior latching element 43 in the form of latching hook 44. An essential feature of the embodiment according to FIG. 6, in comparison with the previously described embodiment, is biasing device 66, by means of which shaft coupling piece 63 of drive shaft 8 on the attachment brush is clamped onto shaft coupling piece 69 of drive shaft 5 on the handle. Similar to the previously described embodiment, here the two shaft coupling pieces 63 and 69 comprise clamping mating surfaces 65 and 73 that are inclined at an acute angle to the longitudinal direction, and that can likewise be set at an angle of greater than about 7 degrees. As FIG. 6 shows, shaft coupling piece 63 on the attachment brush is integrally formed on the associated drive shaft 8 by a spring device 67 in the form of a molded-on compression spring that has a plurality of spring clips that run diagonally. In this way, shaft coupling piece 63 is axially displaceable against the force of spring device 67. When attachment brush 3 is pushed onto handle 2, spring device 67 is so to speak compressed, causing a biasing of shaft coupling piece 63 against shaft coupling piece 69. In this way, the shaft coupling pieces are held firmly against one another. The axial force of spring device 67 is advantageously compensated by the latching connection in the interior of neck 4 of the handle.

Figure 7:
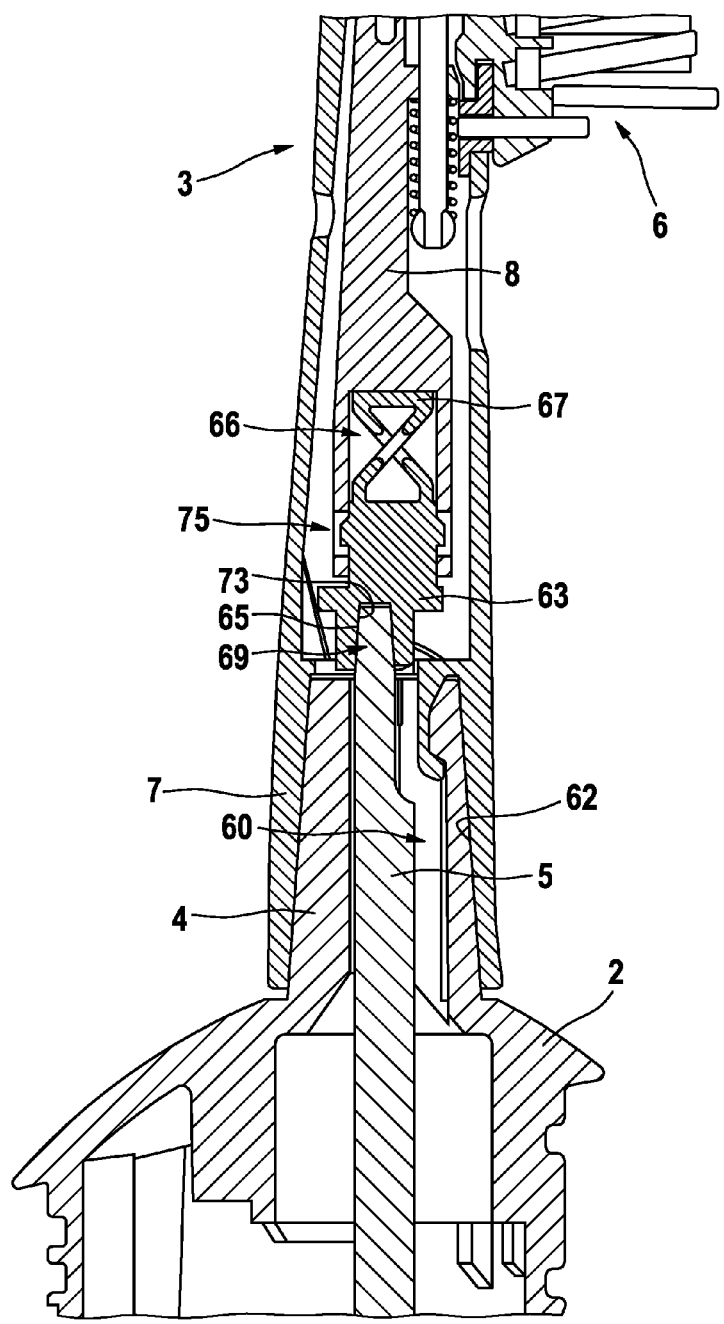
FIG. 7 is a partial sectional view of an electric toothbrush in which a separately formed shaft coupling piece is mounted so as to be axially movable on the drive shaft of the attachment brush, and is pre-tensioned via a spring device.

FIG. 7 shows a realization fundamentally similar to that shown in FIG. 6; here, however, no molded-on compression spring is used. Rather, shaft coupling piece 63 is formed separately from drive shaft 8 and is guided in rotationally fixed fashion thereon by a longitudinal guide 75, while remaining axially displaceable. Longitudinal guide 75 can be implemented in various ways, for example as a spline connection that is secured axially against sliding out. Biasing device 66 comprises here as well a spring device 67 that is advantageously formed as a compression spring and that can be accommodated in a blind hole between shaft coupling piece 63 and drive shaft 8 in order to pre-tension shaft coupling piece 63 axially against drive shaft 8. In this way, a function substantially similar to that shown in FIG. 6 can be achieved.

Figure 5:
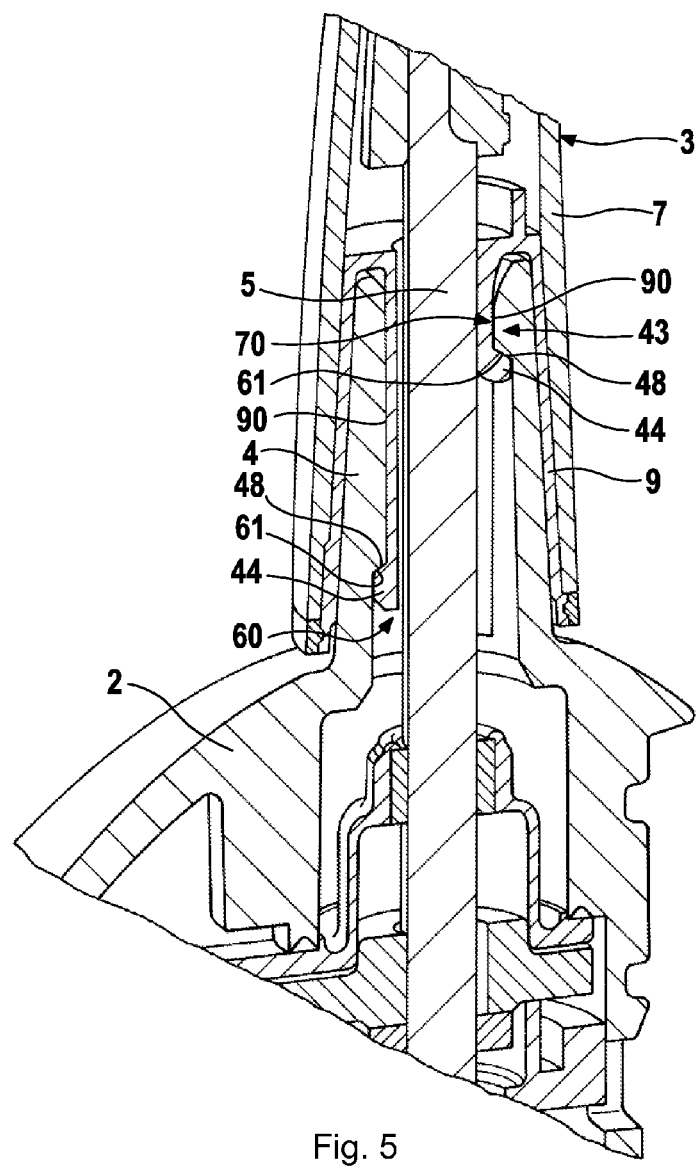
FIG. 5 is a partial sectional view of another embodiment of an electric toothbrush according to which the interior latching element of the attachment brush is formed as a central tubular latching hook that can be pushed over the drive shaft on the handle in the style of a sleeve.

Although it is not separately shown in the Figures, it is also possible to provide, a displaceability and axial biasing of drive shaft 5 of the handle and/or of shaft coupling piece 69 thereof. With regard to the interior latching in interior 60 of neck 4 of the handle, further advantageous specific embodiments may be provided. Thus, for example FIG. 5 shows an interior latching element 43 in tubular connecting piece 7 of attachment brush 3 that is formed as a sleeve or of a tubular central latching hook 44 that can be pushed over drive shaft 5 of handle 2 in the style of a sliding sleeve. This tubular latching hook 44, or the sleeve-type design, can be provided with slits, such that a plurality of latching tongues are provided that can each spring away and can lock transverse to longitudinal direction 12 of attachment part 3, in particular in the radial direction. Complementary to this, the inner wall of neck 4 of the handle comprises a plurality of corresponding latching contours 48.

As FIG. 5 shows, here latching contours 61 on interior latching element 43 can be provided at various axial locations; i.e., latching hooks 44 can have different lengths. In the specific embodiment shown in FIG. 5, tubular central latching hook 44 is provided on previously described coupling insert 9. The latching sleeve can have radial positioning surfaces 90 and can form so to speak a preferably slightly conical centering sleeve that brings about a centering of connecting piece 7 in interior 60 of neck 4 of the handle.

Figure 8:
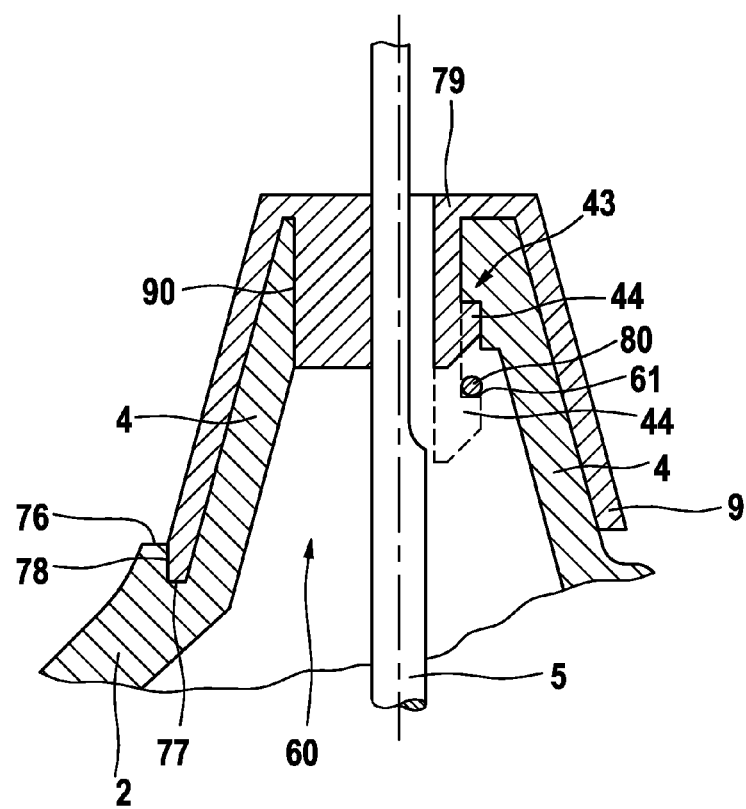
FIG. 8 is a partial sectional view of another embodiment of an electric toothbrush according to which the interior latching element of the attachment brush is integrally formed on a conical coupling ring that surrounds the handle neck internally and externally and is seated with a precise fit and without play on conical surfaces.

FIG. 8 shows another embodiment of interior latching element 43. Here, interior latching element 43 is integrally formed on a profile ring that can be placed into tubular connecting piece 7 of attachment brush 3; this profile ring can form coupling insert 9 described above. This profile ring acting as coupling insert 9 comprises on the one hand a conical outer sleeve that expands toward the end face of connecting piece 7 and is seated with a precise fit on a conically tapering outer surface of neck 4 of the handle. The neck 4 of the handle here comprises, on the end thereof facing the grip portion, a stepped expansion 76 into which there can be worked a pocket 77, in particular a pocket in the shape of an annular groove, into which the outer sleeve section 78 of coupling insert 9 moves with a precise fit. On the other hand, coupling insert 9 comprises an inner sleeve section 79 on which a latching hook is provided in a manner similar to the embodiments described above. Apart from the interior latching hook 44, which can for example be separated by longitudinal slits from the rest of inner sleeve section 79, the inner sleeve section 79 can have a conical external cylindrical surface that is seated with a precise fit on an internal cylindrical surface of neck 4 of the handle, such that tubular connecting piece 7 is held on neck 4 of the handle with a double fit, so to speak.

The engaging by latching hook 44 can take place in the manner described above. Alternatively, instead of a latching projection integrally formed on the wall of neck 4 of the handle, a pin 80 that runs transversely may also be placed into interior 60 of neck 4 of the handle, over which latching contour 61 of latching hook 44 travels and engages. As FIG. 9 shows, the latching connection in interior 60 of neck 4 of the handle can also be reversed. In particular, interior latching means 70 provided on the handle can also comprise a latching tongue in the form of a spring clip that extends substantially parallel to longitudinal direction 12 of neck 4 of the handle and is formed so as to be elastically deformable transverse thereto. In particular, the latching tongue, in the form of spring clip 71, can, as is shown in FIG. 9, spring away and lock in the radial direction, for which purpose a suitable latching contour 48 can be attached on the protruding end of the latching tongue or spring clip 71, for example in the form of a radially inwardly protruding latching projection.

Interior latching element 43 of attachment brush 3 is formed in this arrangement as an inherently rigid projection that protrudes at the end face and is thereby capable of moving into interior 60 of neck 4 of the handle. The projection that forms interior latching element 43 here comprises a latching contour 61 in the form of a latching recess into which the latching projection on spring clip 71 can move.

As FIG. 10 shows, it is also possible to provide a plurality of spring clips 71 in interior 60 of neck 4 of the handle; in the depicted embodiment, these spring clips are integrally formed or fastened on a sleeve-type insert that is seated on neck 4 of the handle. Here, an outer section 82 of insert 81 on the handle neck is put on the external cylindrical surface of neck 4 of the handle and is fixedly locked thereon by latching claws 83. On the outer section 82 of insert 81, there is integrally formed an inner section 84 that extends into interior 60 of neck 4 of the handle, which forms a sleeve-shaped insert that has a cross-section that is not round, on which the latching tongues or spring clips 71 are provided that can spring away transverse to the longitudinal direction of neck 4 of the handle, in particular in the radial direction, and that have corresponding latching contours 61 that are undercut relative to the longitudinal direction, for example, in the form of latching projections. The insert 81 can, for example, be formed as a sheet-metal part, so that spring clips 71 form sheet-metal clips with latching contours 48. Tubular connecting piece 7 of attachment brush 3 can move with the interior latching elements 43 thereof into interior 60 of neck 4 of the handle, similar to the manner shown in FIG. 9, in order to latch with the spring clips 71.

Figure 11:
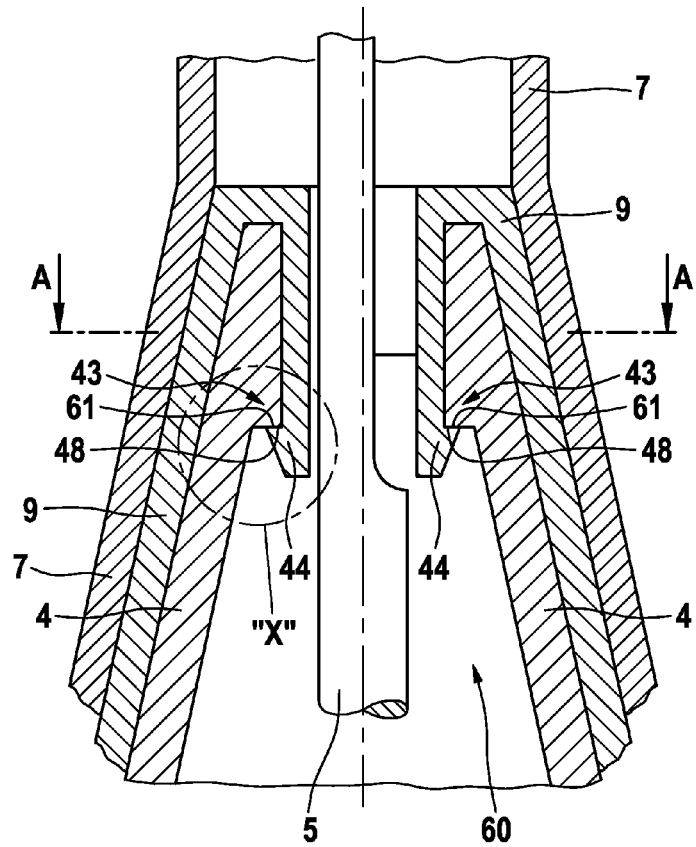
FIG. 11 is a partial sectional view of another embodiment of an electric toothbrush according to which the attachment brush comprises two interior latching elements in the form of flexible latching tongues that have latching contours formed in different ways.
Figure 11:
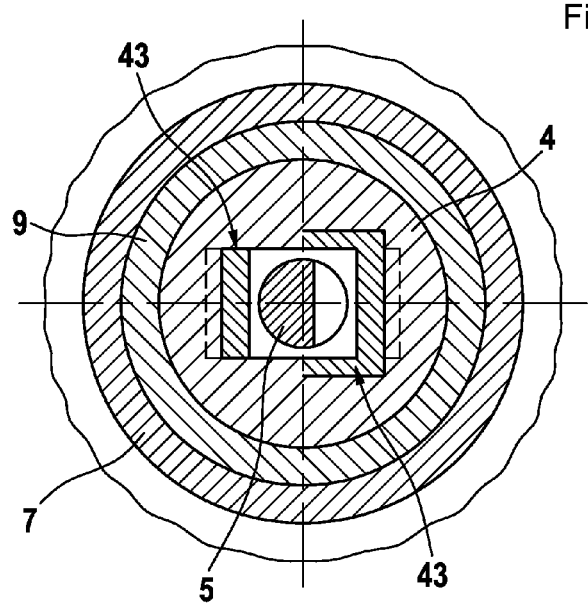
Figure 12:
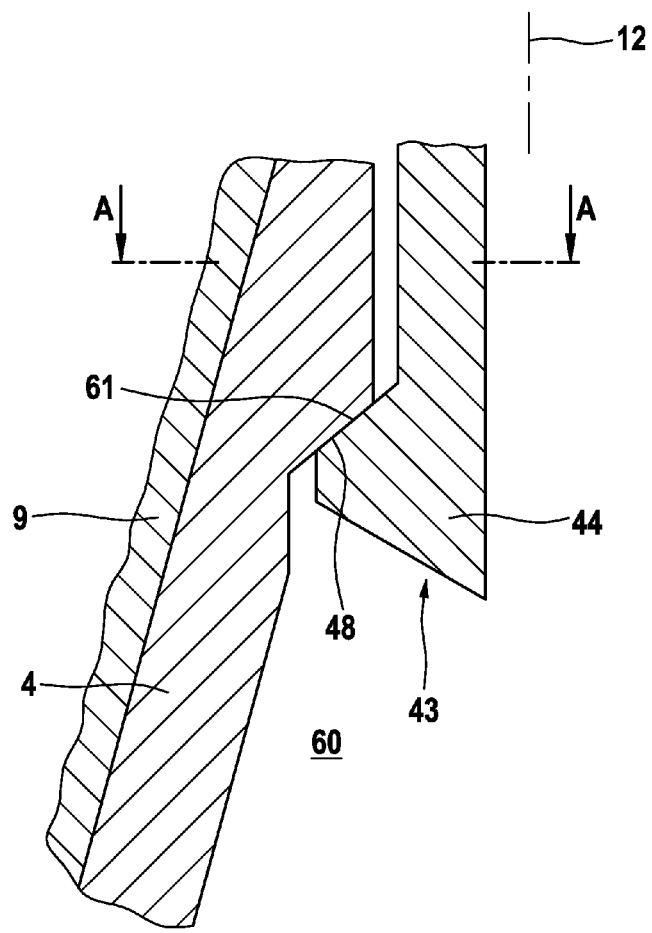
FIG. 12 is an enlarged sectional illustration of the detail marked with "X" in FIG. 11, showing the latching contour of one of the latching tongues.

In order to achieve a radial fixing and, at the same time, an absence of axial play, differently formed interior latching elements 43, or differently formed interior latching means 70, can be used in the interior of neck 4 of the handle. As is shown in FIG. 11, for example on the one hand a latching hook 44 can be provided that has a latching contour 61 that is substantially oriented at a right angle to longitudinal direction 12, the contour engaging with a latching contour 48 on neck 4 of the handle that is also oriented at a right angle to longitudinal direction 12. On the other hand, a latching hook 44 can be provided that has, as latching contour 61, a latching surface that does not run at a right angle to longitudinal direction 12, but rather is inclined thereto at an acute angle, and that locks with a latching surface 48 on neck 4 of the handle that is inclined in complementary fashion thereto at an acute angle. Through such an obliquely positioned pair of latching contours 48 and 61, the latching connection can achieve an axial force component that holds connecting piece 7 of attachment brush 3 on neck 4 of the handle without play. FIG. 12 is an enlarged sectional illustration of the detail marked with "X" in FIG. 11, showing the latching contour of one of the latching tongues.

Figure 13:
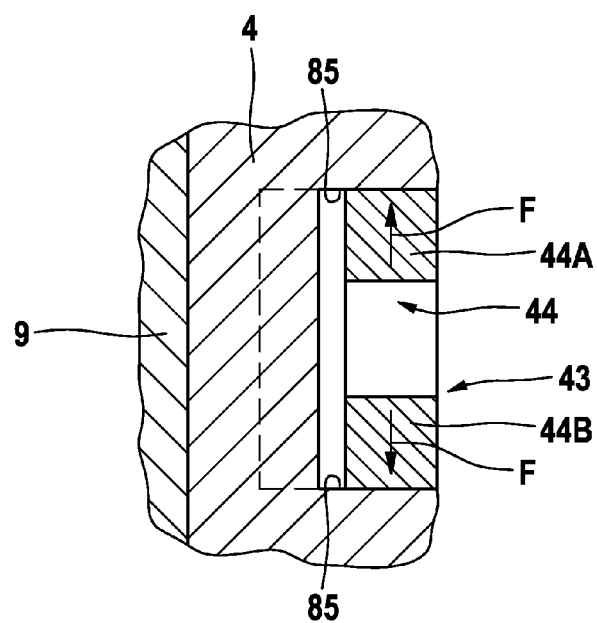
FIG. 13 is a sectional view of the latching tongue from FIG. 12, along the line A-A in FIG. 12.

Alternatively or in addition to a non-round cross-section of neck 4 of the handle and connecting piece 7, a radial movement and/or a movement in the circumferential direction between attachment brush 3 and neck 4 of the handle can be eliminated through a suitable design of the latching connection in interior 60 of neck 4 of the handle. As FIG. 13 shows, for this purpose one of the latching contours, for example latching contour 48 of interior latching means 70 of neck 4 of the handle, can be formed as a pocket that is undercut in the circumferential direction, i.e., that, viewed in the circumferential direction, has beginning and end walls 85. Latching hook 44 can move with a precise fit into a latching recess formed in this way; in this case, latching hook 44 can advantageously have two latching hook parts 44A and 44B that can be spread away from one another and that are applied with positioning surfaces 91 against the limiting surfaces in the circumferential direction. The latching hook parts can for example be clamped pieces that can be extended and that are pre-tensioned away from one another by a spring. Alternatively, a latching tongue divided by a longitudinal slit can also be provided, such that two protruding latching tongue ends are present that move with a precise fit into the pocket-shaped latching recess of latching contour 61 on the inner wall of the handle neck, as is shown in FIG. 13.

Figure 14:
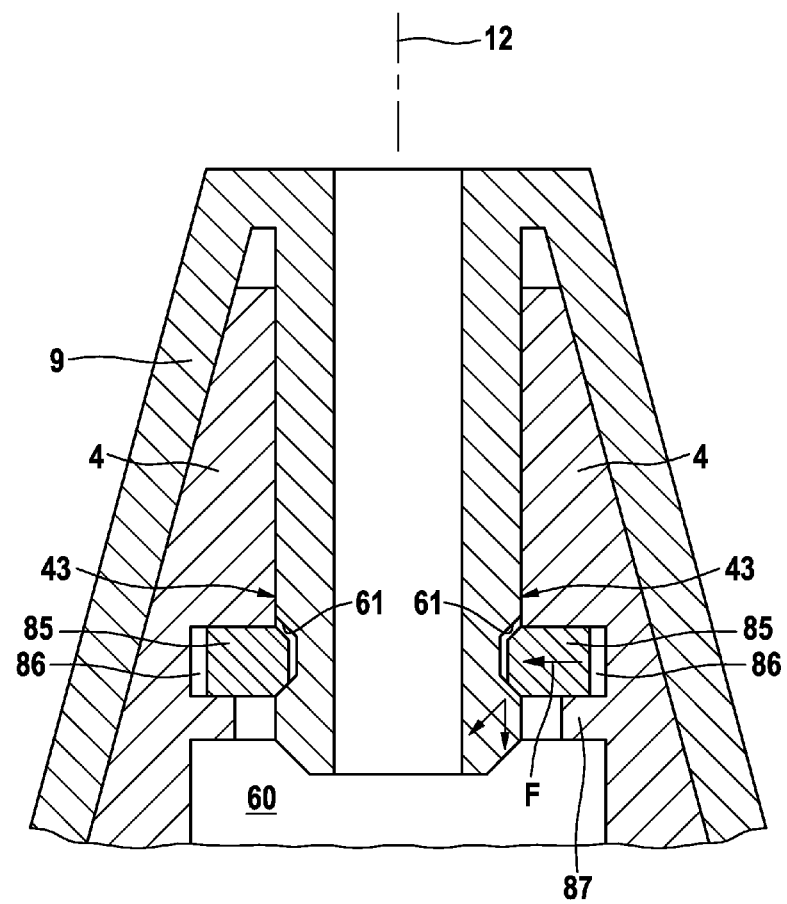
FIG. 14 is a partial sectional view of another embodiment of an electric toothbrush according to which the interior latching means in the interior of the handle neck comprise a clamping ring that is radially inwardly biased for engaging with a tubular interior latching element on the attachment brush.

According to FIG. 14, the latching in interior 60 of neck 4 of the handle can also take place by means of a clamping ring 85 that, in the depicted specific embodiment, is seated in a receptacle pocket 86 in the form of an annular groove in the inner circumferential surface of neck 4 of the handle and that, in the relaxed state, protrudes inward past the internal cylindrical surface. Tension ring 85 is accommodated in receptacle pocket 86 in such a way that it can expand radially, so that the distance by which it protrudes inwardly past the internal cylindrical surface can be at least reduced or removed when the tension ring expands.

Interior latching element 43 provided on attachment brush 3 is formed in this arrangement as a protruding latching sleeve that can be pushed over drive shaft 5 and that has on the outer circumference thereof a latching contour 61 in the form of a circumferential groove that, when the brush is fully pushed on, coincides with receptacle pocket 86, such that tension ring 85 can spring into the circumferential groove of latching contour 61. Here the latching surfaces of tension ring 85 and/or the circumferential groove on interior latching element 43 are inclined at an acute angle to longitudinal direction 12, or are formed in the style of wedge surfaces in order to achieve a connection that is axially free of play. The latching sleeve can have conical outer surfaces and/or can form a radial centering sleeve in order to also radially support connecting piece 7.

As FIG. 14 shows, receptacle pocket 86 can be bounded at the one end by a fixing ring 87 that axially fixes clamping ring 85. Alternatively to the embodiment shown in FIG. 14, the arrangement can also be reversed, in particular in such a way that clamping ring 85 can be seated in and can spring into a receptacle pocket 86 in tubular interior latching element 43, and can spring or latch by expansion into a circumferential groove in the internal cylindrical surface of neck 4 of the handle.

Figure 15:
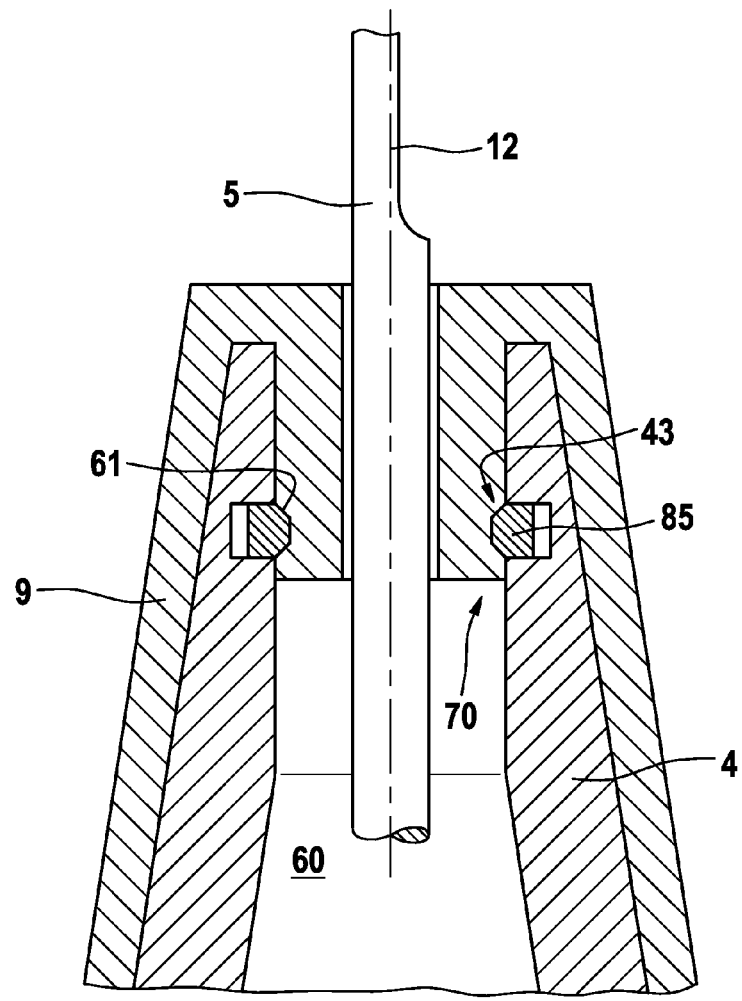
FIG. 15 is a partial sectional view of another embodiment of an electric toothbrush according to which a radial fixing of the attachment brush is provided by means of a clasp-type clip element in the area of the latching connection.
Figure 15:
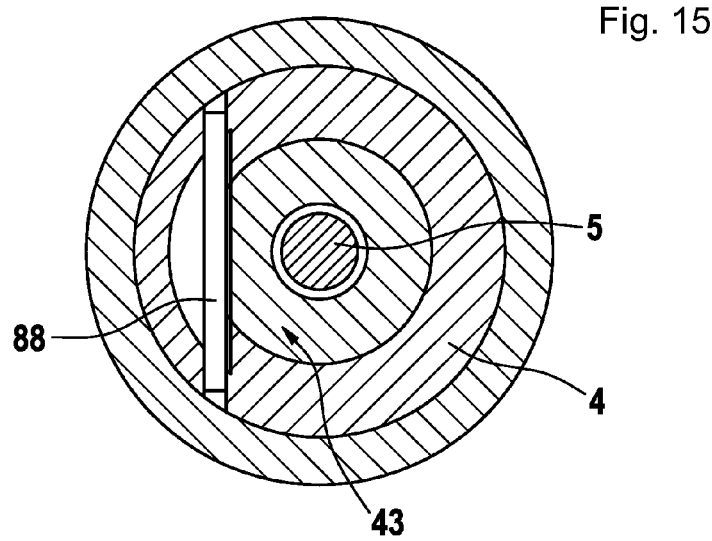

FIG. 15 shows a similar design of the latching connection in interior 6 by means of a clamping ring 85. In order also to realize a securing against rotation in the latching connection, a spring element 88 can be provided that extends transversely and that deviates from the circular ring shape, and is advantageously arranged tangentially; this spring element can spring into a latching groove that is formed so as to match the spring element.

FIG. 16 shows another embodiment, according to which in interior 60 of neck 4 of the handle there is provided a spring clip 71 that is fastened to neck 4 of the handle and that extends substantially in the axial direction as a latching tongue that has a latching projection provided on the protruding end thereof, the projection being formed by a U-shaped angle of the spring clip. Here, tubular connecting piece 7 of attachment brush 3 also comprises an interior latching element 43 that protrudes toward the end face and that moves into neck 4 of the handle. Latching element 43 can form a profile ring having an external cylindrical surface section 89 that moves with a precise fit into an internal cylindrical surface section of neck 4 of the handle. In particular in conjunction with a conical design of the external cylindrical surface of neck 4 of the handle, and an outer coupling piece 62 formed complementary thereto, a radial fit free of play can be achieved in this manner.

In order to achieve a fixing that is also axially free of play, latching contours 48 of spring clip 71 of interior latching means 70 and latching contour 61 of interior latching element 43 can be matched to one another in a suitable manner. In particular, the latching projection, formed by the U-shaped curvature of spring clip 71, of interior latching means 70 can move into a latching recess on interior latching element 43 that is in itself too small for the U-shaped bend. When spring clip 71 snaps into the latching recess on interior latching element 43, the spring clip is pressed on both sides against the edges of the latching recess, resulting in an axial fixing free of play. The above design can also be reversed; i.e., a corresponding projection is provided on interior latching element 43, onto which the U-shaped part of spring clip 71 snaps. An axial fixing, free of play, of attachment brush 3 can be achieved by two tapered or obliquely positioned bevel surfaces or wedge surfaces on spring clip 71, as well as complementary conical and/or bevel surfaces on interior latching element 43, and the elastic pressing together thereof.

FIG. 17 shows a further embodiment, according to which neck 4 of the handle and tubular connecting piece 7 do not form closed annular profiles, but rather each form half-shell-shaped coupling pieces 68 that can be placed together so as to complete one another such that a fastening of attachment brush 3 is achieved in a manner preventing it from rotating. More precisely, here neck 4 of the handle can form a half-shell-shaped coupling piece 68 that moves into tubular connecting piece 7 of attachment brush 3. Inward-projecting coupling flanges 98 are provided in the connecting piece 7 that move onto the edges of half-shell-shaped coupling piece 68. Advantageously, here the edge end surfaces of the half-shell-shaped coupling piece, and/or the engagement projections that move into engagement therewith of connecting piece 7, are provided with a centering contour 97, for example in the form of a V-shaped groove or dovetail profile, in order to bring about a centering of neck 4 of the handle in connecting piece 7. Here, half-shell-shaped coupling piece 68 is thus on the one hand surrounded on the circumference thereof by connecting piece 7, and on the other hand is supported in centering fashion at the edge ends. Alternatively, or in addition, a centering can also take place on the end face of neck 4 of the handle. Advantageously, here a half-ring-shaped centering contour can be provided on connecting piece 7 and on the end face of half-shell-shaped coupling piece 68, for example in the form of a V-shaped groove and/or a dovetail profile.

In a reversal of the arrangement shown in FIG. 17, connecting piece 7 may also include half-shell-shaped coupling piece 68, which is then pushed onto neck 4 of the handle in a complementary manner. As FIG. 17 shows, here as well a latching connection arranged in interior 60 of neck 4 of the handle is provided by a latching hook 44.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An attachment part for an electric toothbrush, comprising:
a brush head, a tubular connecting piece for connecting to the brush head to a neck of a handle of a toothbrush, and a drive shaft for driving the brush head, wherein the connecting piece has at least one interior latching element that is arranged to move into the interior of the neck of the handle and to create a disengageable connection of the attachment part to the neck of the handle, the interior latching element being radially inwardly offset, relative to an internal cylindrical surface of the connecting piece, such that a gap remains between the exterior of the interior latching element and the internal cylindrical surface, the gap being suitably made such that a wall of the neck of the handle can be moved into the gap.

2. The attachment part according to claim 1, wherein the interior latching element has at least one latching tongue that extends in the direction toward the end face of the connecting piece, the latching tongue having a latching contour.

3. The attachment part according to claim 2, wherein the latching contour of the latching tongue is arranged at various axial positions.

4. The attachment part according to claim 2, wherein the latching contour is arranged on the radially outward-facing side of the interior latching element.

5. The attachment part according to claim 1, wherein the interior latching element has an undercut in the circumferential direction for preventing the attachment part from rotating on the neck of the handle.

6. The attachment part according to claim 1, wherein the drive shaft has a shaft coupling piece that is suitable for coupling to a drive shaft on the grip portion, and the shaft coupling piece has a conical clamp mating surface.

7. The attachment part according to claim 6, wherein the clamp mating surface is inclined at a tapered angle of greater than about 3.5 degrees to the longitudinal axis of the drive shaft.

8. The attachment part according to claim 1, wherein the drive shaft is movably mounted in the axial direction relative to the tubular connecting piece.

9. The attachment part according to claim 8, wherein a biasing device is provided for biasing the drive shaft toward the end face of the connecting piece.

10. A handle of an electric toothbrush having a grip portion and having a neck of the handle having a coupling device that is suitable for coupling an attachment part according to claim 1, and having a drive shaft that is suitable for driving the attachment part, wherein the neck of the handle has an internally arranged latching means for engaging with an element of the attachment part that can be moved into the interior of the neck of the handle.

11. The toothbrush handle according to claim 10, wherein a shaft coupling piece of the drive shaft has a conical clamp mating surface.

12. The toothbrush handle according to claim 11, wherein the clamp mating surface is inclined relative to the longitudinal direction of the drive shaft at a tapered angle of greater than about 3.5 degrees.

13. The toothbrush handle according claim 11, wherein the drive shaft is movably mounted in the axial direction relative to the neck of the handle.

14. The toothbrush handle according to claim 13, wherein a biasing device is provided for biasing the drive shaft away from the handle.

15. The toothbrush handle according to claim 10, wherein a coupling device having at least one engagement part that is suitable for engagement with the tubular connecting piece of the attachment part is provided on the neck of the handle, the coupling device having a coupling piece that is axially movable in the longitudinal direction of the handle.

16. The toothbrush handle according to claim 15, wherein the coupling piece is formed such that an axial movement of the coupling piece produces a transverse movement of the engagement part transverse to the longitudinal direction of the handle.

* * * * *